(12) United States Patent
Schulz (10) Patent No.: US 9,072,616 B2
(45) Date of Patent: Jul. 7, 2015

(54) DEVICE FOR MOVING AND HOLDING OF A FINGER TIP

(76) Inventor: Stefan Schulz, Karlsruhe (DE)

( * ) Notice: Subject to any disclaimer, the term of this patent is extended or adjusted under 35 U.S.C. 154(b) by 0 days.

(21) Appl. No.: 13/571,835

(22) Filed: Aug. 10, 2012

(65) Prior Publication Data

US 2013/0041476 A1 Feb. 14, 2013

(30) Foreign Application Priority Data

Aug. 13, 2011 (DE) .......................... 10 2011 110 101

(51) Int. Cl.
| | | |
|---|---|---|
| *A61F 2/48* | (2006.01) | |
| *A61F 2/54* | (2006.01) | |
| *A61F 2/68* | (2006.01) | |
| *A61F 2/58* | (2006.01) | |
| *A61F 2/70* | (2006.01) | |
| *A61F 2/50* | (2006.01) | |
| *A61F 2/76* | (2006.01) | |

(52) U.S. Cl.
CPC ............. *A61F 2/68* (2013.01); *A61F 2002/704* (2013.01); *A61F 2002/6818* (2013.01); *A61F 2002/5038* (2013.01); *A61F 2/586* (2013.01); *A61F 2002/5079* (2013.01); *A61F 2002/701* (2013.01); *A61F 2002/762* (2013.01); *A61F 2002/7625* (2013.01); *A61F 2002/7635* (2013.01); *A61F 2002/764* (2013.01); *A61F 2002/7645* (2013.01)

(58) Field of Classification Search
USPC .......... 623/24, 57, 64, 63; 901/31, 32, 36, 38, 901/39
See application file for complete search history.

(56) References Cited

U.S. PATENT DOCUMENTS

| | | | | |
|---|---|---|---|---|
| 3,418,661 | A * | 12/1968 | Allison et al. .................. | 623/25 |
| 4,598,942 | A * | 7/1986 | Shum et al. ................... | 294/106 |
| 5,888,213 | A * | 3/1999 | Sears et al. ..................... | 623/24 |
| 6,846,331 | B2 * | 1/2005 | Senoir ............................. | 623/57 |
| 2005/0021154 | A1 * | 1/2005 | Brimalm ......................... | 623/64 |
| 2010/0036507 | A1 * | 2/2010 | Gow ................................ | 623/64 |
| 2010/0191343 | A1 * | 7/2010 | Puchhammer et al. ..... | 623/21.15 |
| 2011/0144770 | A1 * | 6/2011 | Moyer et al. ................... | 623/64 |
| 2012/0221122 | A1 * | 8/2012 | Gill et al. ........................ | 623/64 |

FOREIGN PATENT DOCUMENTS

| | | |
|---|---|---|
| EP | 0748194 B1 | 7/1998 |
| EP | 1962731 B1 | 11/2009 |
| EP | 2135588 A2 | 12/2009 |
| WO | WO2010/149967 A1 * | 12/2010 |

OTHER PUBLICATIONS

Step Motor Basics Guide; www.geckodrive.com/support/step-motor-basics.html; accessed Nov. 22, 2013; pp. 1-10.*
Cranny et al., Thick-film force, slip and temperature sensors for prosthetic hand, Mar. 4, 2005, Institute of Physics Publishing, Means. Sci. Technol. 16, pp. 931-941.*
Erickson et al., A Novel Single Digit Manipulator for Prosthetic Hand Applications, Apr. 9, 2007, State University of New Jersey, pp. 1-5.*

* cited by examiner

*Primary Examiner* — Marcia Watkins
(74) *Attorney, Agent, or Firm* — Davis & Bujold, P.L.L.C.; Michael J. Bujold (57) ABSTRACT

A method for movement of at least a finger limb whereby, in order to maintain a position of the finger limb, the electric motor is supplied with a current. In order to maintain a position of the finger limb, the electric motor is supplied the with less energy than the current which is supplied to the electric motor for moving the finger limb.

17 Claims, 5 Drawing Sheets

FIG. 9

DEVICE FOR MOVING AND HOLDING OF A FINGER TIP

This application claims priority from German Application Serial No. 10 2011 110 101.6 filed Aug. 13, 2011.

FIELD OF THE INVENTION

The present invention concerns a method for moving of at least one finger limb.

In addition, the present invention covers a finger limb which comprises of an electric motor for movement of the finger limb and a control and/or regulating element which at least controls and/or regulates an electric current characteristic, such as the current level, voltage and/or the frequency of the current which is supplied into the electric motor.

BACKGROUND OF THE INVENTION

Finger limbs are applied in the field of robotic and/or prosthetic to duplicate the function and/or look of natural, especially human finger limbs. Such finger limbs are movable mounted to a basic element. The basic element hereby serves for the attachment of the finger elements, comprising of the finger limb, to a body part, especially to a hand and or an arm part. An electric motor is used for movement of the finger limb relative to the basic element. Hereby, the electric motor can be positioned in the finger limb or outside of the finger limb, for instance at or in the basic element.

If the finger limb needs to be moved, an electric motor, designed as a DC motor, as an electrically commutated motor, or a stepper motor, is supplied with a continuous or pulsed current so that the output shaft moves, especially pivots, the finger limb via a transmission such as a planetary gear, a spur gear, a bevel gear, and/or a worm gear, a head screw, a friction gear transmission and/or through driving rods, belts and/or chains.

There are, however, situations in which the finger limb needs to be maintained in a position. This holding can take place against an outer force as it happens during the holding of a holding rod, whereby the weight of the person during the holding moves into the hand. It can also be desired to maintain a position without having a significant external force affecting the finger and/or the finger limb.

EP 0748194 shows a finger element in which the movement of the electric motor is transferred, via a worm gear transmission, to a pivoting movement of the finger limb. The intention is to create a self locking for keeping the finger in its position even against an outside force.

Known through EP 0748 194 B1 is an electrically operated hand prosthesis in which the drive motor, which moves the finger, is positioned in the finger. In accordance with the approach to the solution which is discussed here, the motor axle has a worm shaft which meshes with a respective worm gear wheel which is stationary positioned in the support body of the prosthesis. The proposed worm gear wheel/worm shaft combination has the alleged advantage that this transmission is a locking transmission in which the finger is locked in its position without a motor drive.

EP 1962731 and EP 2135588 show a finger limb in which a worm gear transmission is applied for self locking, whereby the worm gear wheel is linked to the basic element via a bevel gear transmission.

SUMMARY OF THE INVENTION

It is the task of the present invention to create a method and a device which enables an appropriate movements and holding of a finger limb.

The task is solved through a device and a method in accordance with the invention.

The task is especially solved through a method for moving at least one finger limb whereby an electric motor is supplied with current to maintain a finger position. This current is hereby larger than 0 and supplies the electric motor with lesser energy than the current which supplies the electric motor for the movement of the finger limb.

Thus, it was discovered that the electric motor, for holding the finger limb, can be applied with a lesser current, a lesser current frequency, a lesser voltage and/or with a current with different characteristics, so that the electric motor is, however, supplied with energy but with lesser energy during a time interval as for the movement of the finger limb.

It was also discovered that, instead or in addition of a self locking transmission, such as a worm gear transmission, the electric motor can be used as a brake.

Through the use of the electric motor as a decelerator of finger limb movement, it is not necessary to apply transmissions with self locking features. Thus, a much larger variety of different transmissions can be utilized.

Transmissions with an increased self locking feature have a much worse efficiency so that, during the movement of the finger via the self locking transmission, an increased level of energy has to be applied. This fact leads to the necessity of the application of stronger and larger motors, stronger and therefore larger energy storage, and stronger bearings for the motor and the transmission. Thus, the finger becomes heavier, bulky and operation of the finger is only possible for a limited time because of the limited energy storage capacity.

Through the locking of the finger movement by means of an electric motor, the self locking of the transmission can be omitted and a smooth moving transmission can be used. Such transmissions can be bevel gear transmissions, bevel screw transmissions, spur gear screw transmissions, friction gear transmissions, globoid transmissions.

Through the application of a transmission with low self locking, the stiffness of the finger can be designed in a way that the finger gives in when a larger, outer force affects the finger. Also, the application of the electric motor as a brake for movement of the finger creates the realization of a different finger stiffness. This finger stiffness can be matched to the bearer, to the finger and/or to the respective used situation. The matching can be accomplished through the amount of the energy which is supplied to the motor.

It is therefore also possible to move the different fingers into a position in which the fingers create a hook for a handle, such as hooking into a handle of a suitcase. When lifting the suitcase and not all fingers are covering the handle, the load is distributed in this case just to the fingers which cover the handle. If the transmission here has a strong self locking, the load needs to be created by the covering fingers whereby the fingers can get damaged. If a transmission is used which has a lesser self-discovery, the handle covering fingers will slightly give in until the load is distributed to several or all fingers.

Also, during a fall or other situations in which the finger can get damaged, the brake can be designed in such a way that the finger gives in and does not get damaged.

It was also discovered that the electric motor needs to have less current supplied to decelerate a finger limb than for the movement of a finger limb. Thus, for executing movement of the finger, a current is supplied to the electric motor. If just a low current is supplied to the electric motor, the electric motor cannot overcome the friction load of the transmission, and/or the joints and/or other moving parts and the finger limb can be maintained in the momentary position without any motion.

Preferably, the electric motor can be positioned in the finger limb. Thus, a slimmer basic element can be created because the basic element does not need any or few electric motors. That provides the basic element with a more natural look.

Rotating motion of the shaft of the electric motor can be transferred to a bevel gear, whereby the bevel gear meshes with a second bevel gear and the second bevel gear is fixedly connected with the pivoting axis. A so-called bevel gear transmission has only a low self locking and transfers the torque of the electric motor to the basic element which is fixed connected with the body and/or machine part.

The second bevel gear can also be fixedly connected with a second finger limb so that the first finger limb can move with reference to the second finger limb.

Preferably, the movement of the finger limb and/or the finger and/or the gear wheel and/or the motor shaft and/or the transmission shaft is captured by means of a motion sensor. Hereby, the motion sensor or the motion sensors can be positioned in the joints or at other places of the finger limb, such as the finger limb tip. The motion sensors can also be positioning sensors, acceleration sensors, direction sensors and rotation speed sensors, force sensors, torque sensors, or the like.

Preferably, the finger limb and/or the finger element can comprise of an electric motor, a control and/or sensors and/or a regulation of the electric motor, a battery and/or a transmission. Thus, the finger element can be attached to the basic element without the need to interconnect several other elements. The finger element can have an assigned input, such as an electric input through which an electric control signal is sent to the control and/or regulation. Such a control signal can be considered as a muscle potential.

The current is preferably increased if the finger limb unintentionally moves. Thus, the electric motor receives just a low current for the holding of the finger limb, so that in total the energy consumption remains as low as possible. If the low current is not sufficient for the holding of the finger limb and the finger is moving, the current will be increased so that the finger limb reliably remains steady. If the finger limb moves, although it is intended to keep it in a certain position by means of the electric motor, the current which is supplied at that time to the electric motor can be reduced. Prior to the correction of the current, a position correction can be executed by activating the electric motor and thus the finger limb.

Preferably, the holding current of the electric motor is lower than a factor 0.9, especially preferred more than the factor 0.5, especially lower than the factor 0.1 of the current which is needed to move the finger limb.

Preferably, the finger limb comprises of an electric motor for the movement of the finger limb, and a control and/or regulation element which controls at least one current characteristic, such as the current strength, voltage, and/or frequency of the current which is supplied into the electric motor, whereby the control and/or regulation element provides a current for the electric motor which is needed for movement or holding of the finger limb, but for holding of the finger element, the controlled and/or regulated current characteristic is established in such a way that the electric motor receives less energy.

The electric motor can hereby have a functional connection with a bevel gear and the bevel gear meshes with a second bevel gear, whereby the second bevel gear is fixed connected, relative to the finger limb, with a pivotable element and the rotation axis of the second bevel gear is the pivoting axis of the finger limb.

The rotation axis of the second bevel gear can be positioned vertically with reference to the rotation axis of the first bevel gear. The axes of the bevel gears can be present in one plane, but can also be positioned with an offset with respect to one another, by modification of the tooth shape of the gear.

Preferably, an additional finger limb can also be linked with an additional finger limb, especially mechanically or magnetically, so that the additional finger limb also moves when the first finger limb moves. The second finger limb can be positioned at the finger element of the first finger limb or at an additional, preferably neighboring, finger element.

Preferably, the additional finger element has a battery through which the electric motor of the first finger element is supplied. In addition, the additional finger element can have a control/regulation for the control/regulation of the electric motor of the first finger limb.

An additional embodiment comprises of a prosthesis with at least a finger limb, a positioned motor in it to drive the finger limb as well as a prosthesis basic part around which the finger limb pivots, whereby a non-locking transmission is positioned between the finger limb and the basic part.

BRIEF DESCRIPTION OF THE DRAWINGS

In the following, the invention is further explained based on an embodiment and the support of the drawings.

Hereby shows.

DETAILED DESCRIPTION OF THE PREFERRED EMBODIMENTS

Figure 1:
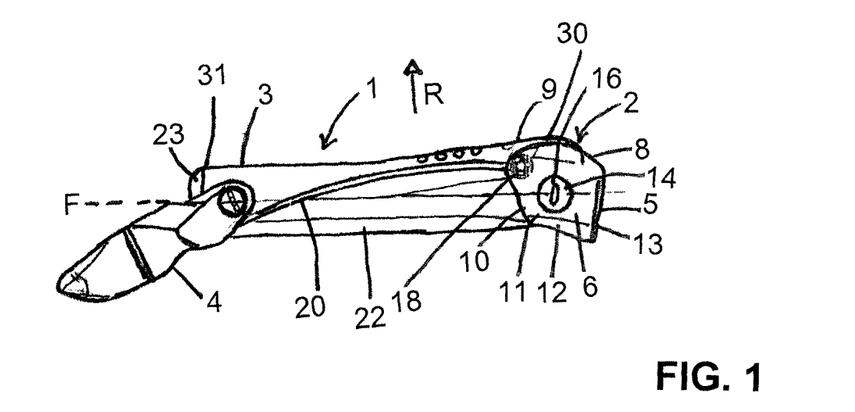
FIG. 1 a side view of a finger element.

FIG. 1 shows a finger element 1 comprising of a basic element 2, a first finger limb 3 and a second finger limb 4. The finger element 1 is hereby designed as a copy of a natural human finger. The basic element 2 is designed to be attached directly to a human body part, especially to a hand stump, and is preferably designed to be attached to a bracket which is connected with a body part. The first finger limb 3 is pivotable connected, by its proximate end 30, with the basic element 2. The second finger limb 4 is pivotable connected to a distal end 31 of the first finger limb 3.

Figure 2:
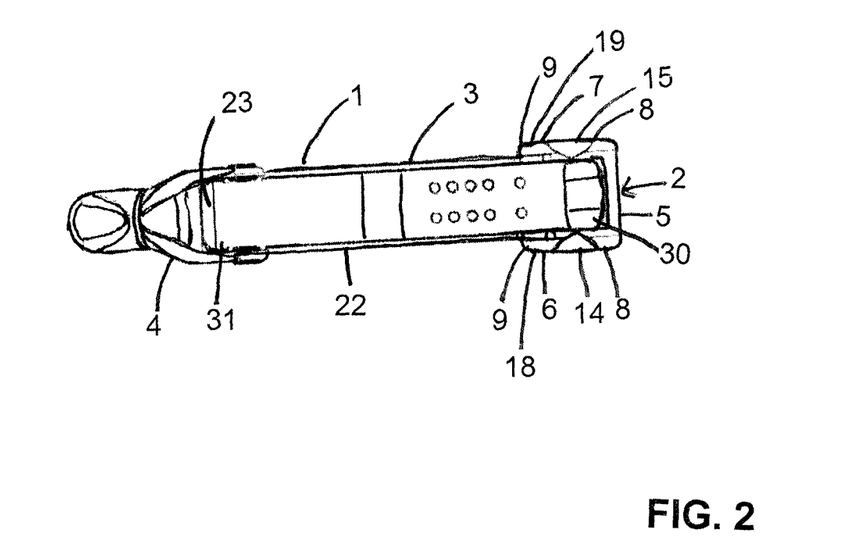
FIG. 2 a top view of the finger element of FIG. 1.

The basic element 2, as shown closer in FIG. 2, has an approximate shape of a horse shoe to accommodate the proximal end of the first finger limb 3. Also, the basic element 2 has a first straight plane 5 which connects segments 6 and 7 and thereby forms the horse shoe shape.

The straight plane 5 hereby enables that the basic element 2 can be connected with a bracket.

The segments 6 and 7 are plate-shaped and each primarily extends in a plane in which the main extension direction of the finger element 1 is incorporated or where it is in parallel thereto. The plane surface 5 runs primarily perpendicular to the segments 6 and 7. The segments 6 and 7 have each a bent convex shape upper edge 8 which extends in a direction of the distal end of the first finger limb 3, via a rounded edge 9 and converts primarily into a straight extending front edge 10. The front edge 10 converts, via a second rounded corner 11, into a rounded lower edge 12. The lower edge 12 borders with the rear edge 13 which is designed straight so that it can hold at a bracket. The basic element 2 has a recess 14 and 15 in each of the segments 6 and 7 through which an axle can be pass through, in each case, around which the first finger limb 3 pivots.

In the area of the front corner 9, the segments 6 and 7 have each another recess 14, 15 were a spring 20, 21 can be pivotable attached to. The basic element 2 hereby is preferably manufactured from metal, like steel, titanium and/or aluminum, but can also be constructed from plastic and/or compound material such as fiber glass reinforced or carbon fiber reinforced plastic. The springs 20, 21 are also preferably made from spring steel, a NiTi alloy and/or titanium. The springs 20, 21 have a curve shaped pattern.

Figure 3:
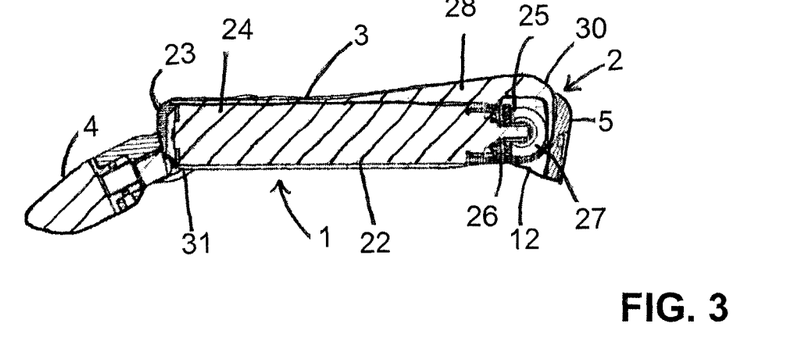
FIG. 3 a side, section view of the finger element of FIG. 1.

The first finger limb 3 comprises an enclosure 22, a cover 23, an electric motor 24 with a transmission, a transmission output shaft 25, a first bevel gear 26, and a second bevel gear 27. The enclosure is made as one piece from a material such as titanium, aluminum, plastic or steel and is close to a cylindrical shape, whereby the cylinder main axis Z extends itself along the finger limb main axis F. In a direction R, perpendicular to the finger limb main axis F and the pivot plane of the finger limb 3, the shape of the enclosure 22 deviates from a cylindrical shape. Here, the enclosure 22 has a thickening 28 at its proximal end towards the top. The thickening 28 increases from a distal to a proximal. The thickening can be designed as either an increase of the wall thickness in this area, through a change of the inner space shape but maintaining the wall thickness, or through an additional, separate cavity. Batteries or other power storage devices, which supplies the motor in the cavity of the finger limb or in a neighboring finger limb, can be placed in such a cavity. It is also possible to accommodate one or several other circuits in the cavity.

At the proximal end 29, the enclosure 22 has a closed or substantially closed end 29. The closed end 29 hereby transitions, by means of the rounding 30, into the thickening 28. The cavity of the enclosure 22 can be protected against external influences by the closed end 29. The rounding 30 is hereby matched to the upper edge 8 of the basic element so that the upper edge 8 of the basic element mainly terminates with a rounding.

Thus, the finger is further designed like the natural structure because the perimeter increases in the direction towards the hand and finally ends in an ankle shape.

As it can also be seen in FIG. 3, the bottom part of the enclosure has an area of concavity so that also the bottom part of the enclosure 22 which deviates from the cylindrical shape. The area of concavity of the enclosure 22 is matched to the lower edge 12 of the basic element so that the lower edge 12 of the basic element can connect with an outer side of the first finger limb. The enclosure 22 has an opening, at the distal end, which leads into the cavity of the enclosure 22. The opening and the cavity are dimensioned in such a way that the electric motor can be brought into the cavity through the opening. The opening can be blocked with a cover 23 so that the electric motor and/or the transmission, within the cavity, can be protected against external influences. The cover is hereby preferably made from plastic and can be clipped to the opening. Preferably, the cover ends with the outer area of the first finger limb so that the edges of the enclosure 22, at the distal end, are surrounded by the cover. If the finger limb or the entire finger element is put into a casing, such as a glove, the edges of the finger limb or finger element, respectively, will not destroy the fibers of the casing.

Figure 4:
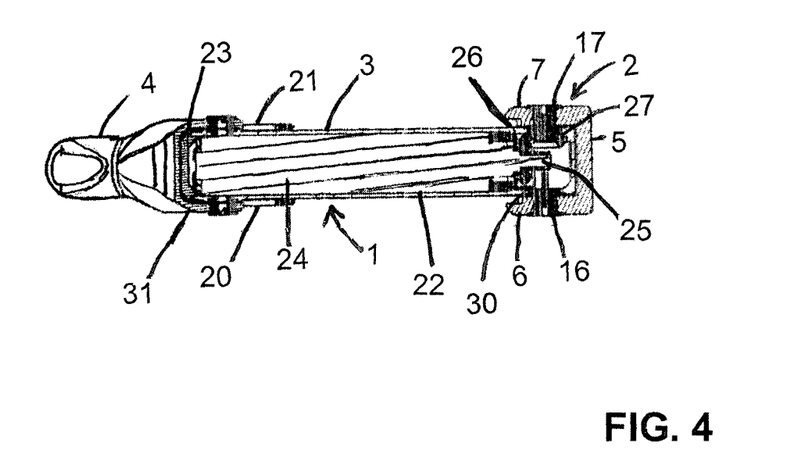
FIG. 4 a top, section view of the finger element of FIG. 1.
Figure 5:
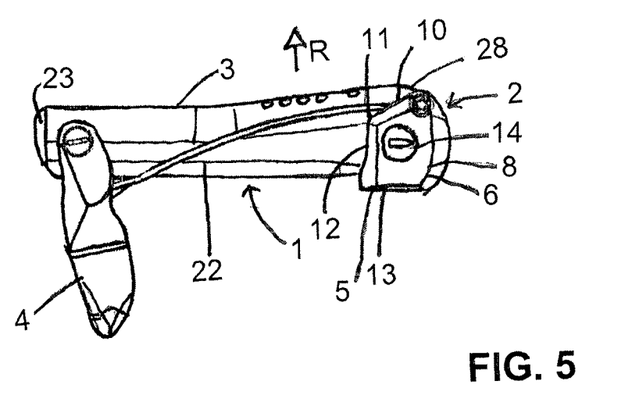
FIG. 5 the finger element of FIG. 1 in an angled position.
Figure 6:
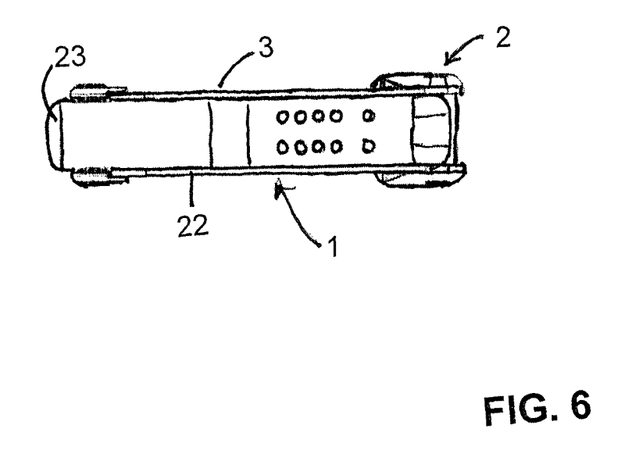
FIG. 6 a top view of the finger element of FIG. 5.
Figure 7:
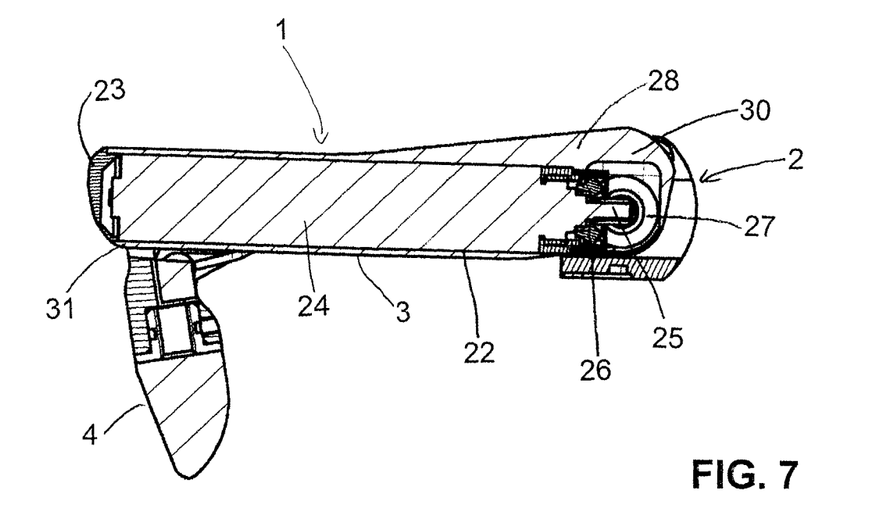
FIG. 7 a section view, from the side, of the finger element of FIG. 5.
Figure 8:
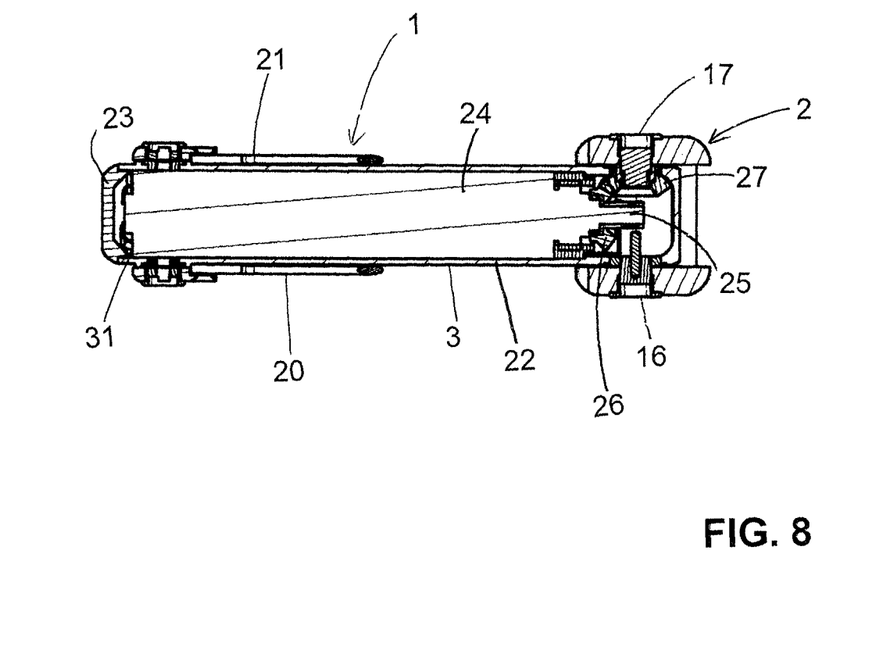
FIG. 8 a top view of the finger element of FIG. 7.

The electric motor is positioned within the cavity of the enclosure 22. The electric motor itself hereby extends along a main extension direction Z of the finger limb and has a transmission with which the electric motor is integrated, and the transmission has an output shaft which is functionally linked with an output shaft of the electric motor, and the rotation of the output shaft of the electric motor is transferred to the bevel gear. The rotation axis of the bevel gear, therefore, runs coaxial or parallel with the main extending direction of the finger limb. A second bevel gear is present vertical to the first bevel gear and meshing with it. The rotation axis of this second bevel gear is vertical with reference to the plane of one of the segments of the basic element. The bevel gear is rotation-proof mounted by means of a bolt to the segment. At the opposite segment of the basic element, axially flush with the first bolt, an additional axle or bolt 16 is provided which serves as pivoting axis for the first finger limb. If the first bevel gear is driven by the electric motor, via the transmission, the first bevel gear supports itself with the second bevel gear and the first finger limb pivots together with its connected second finger limb around the pivoting axis which is determined by the bolt 16.

A second pivotable finger limb is connected at the distal end of the first finger limb. Hereby, the second finger limb has two sections which each are pivotable connected at one side of the first finger limb. The pivotable connection is hereby positioned at the distal end of the finger limb, mainly at one half of the height of the finger limb. The pivotable connection hereby comprises a recess, each positioned on one side of the enclosure 22, and a recess at each of one section, whereby each recess on one side is connected with a recess of the enclosure through one or several connecting elements, such as axles or bolts. This connection, which can be, for instance, realize by a screw, serves as a pivoting axis around which the second finger limb pivots with reference to the first finger limb.

The second finger limb 4 is connected by several, flexible bent springs 20, 21 which are designed, with the basic element, as a rod. The spring can hereby be elastically bent. The rod leads, during a pivoting motion of the first finger limb, to a pivoting motion of the second finger limb relative to the first finger limb. If the second finger limb is moved by a motion or by locking, created by the electric motor, the rod hereby bends and the second finger limb can be spring-loaded, elastically moved. During the movement of the second finger limb, the cover serves as a stop so that the second finger limb cannot include an angle which is lower than a determined limiting angle with reference to the main extending direction of the first finger limb. The connecting locations of the rod have an offset, with reference to the basic element as well as to the second finger element, distal to the respective pivoting axes.

The second finger element has a recess, at its distal end, into which a pin can be inserted so that a cap can be mounted on the finger element. The cap is especially made from plastic and provides a soft fingertip. By an exchange of the fingertips, the length of the finger elements can also be easily changed.

The finger limb comprises of an electric motor which is connected, by wiring, with a control and/or regulation device. The control and/or regulation hereby can be provided with a control and/or regulation input. This control and/or regulation input can, for instance, be connected to a muscle electrode which captures the muscle potential and creates a respective signal as the control and/or regulation input.

Preferably, the control and/or regulation device supplies the electric motor with a current which is provided by a battery. Hereby, the battery is also positioned in the basic element or in an additional bracket. If a signal is now sent through the control and/or regulation input to the input to move the finger limb, a current of a certain amount and direction is provided for the electric motor by the control and/or regulation device. The amount and/or the polarity of the current can depend on the control and/or regulation signal, of previous signals, of the finger tip position, and/or of the finger speed, etc. If the finger now needs to be held in its position, the current which is sent to the electric motor is reduced to 1/10 of the maximal current. If a motion sensor detects still movement of the finger limb, the current will be increased until the finger limb does not move anymore. Hereby, the current has the opposite polarity in comparison to a current which would create the braking movement.

Figure 9:
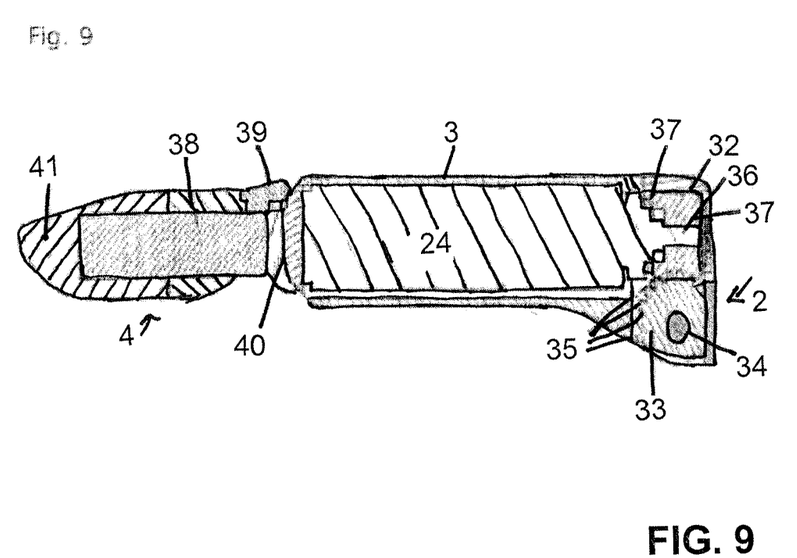
FIG. 9 an additional embodiment of a finger element.

FIG. 9 shows an additional embodiment, of a finger element 1, comprising a first finger limb 3 and a second finger limb 4, whereby the second finger limb 4 is attached at the distal end of the finger limb 3. The first finger limb 3, which can be pivoted around a first joint axis 34, is connected at the basic element 2.

The second finger element 4 comprises of a stiff kernel which serves for the mounting and stabilization of the second finger limb 4. Around the distal area of the kernel 38, the soft and elastic fingertip 41 is positioned. A scraper, which bridges the transition between the first and the second finger limb and which creates an almost steady surface, is positioned between the kernel 38 and the distal end of the first finger limb.

A lock cover or slide surface 40, 23, respectively, is provided at the distal end of the first finger limb 3 to block the enclosure of the first finger limb and to have the second finger limb 4 to slide on it. The cover 40, 23 can also be used as stop for movement of the second finger limb 4.

The first finger limb 3 is driven by a drive 24, such as an electric motor. The electric motor, or the transmission which is directly connected with the electric motor, respectively, comprises of a drive shaft 36, 25 which runs through the guides 37 which serve as bearings. A head screw gear 32, which meshes with a head screw gear segment 33, is torque proof positioned on the drive shaft 36, 25. The head screw gear segment 33 has gear segments 35. The head screw gear segment 33 is positioned at the first joint axis 34 and torque proof connected with the basic element 2.

A head screw transmission can hereby be interpreted as a spur gear with a curved toothing pattern.

REFERENCE CHARACTERS

1 Finger Element
2 Basic Element
3 First Finger Limb
4 Second Finger Limb
5 Plane surface
6 First segment
7 Second segment
8 Upper edge
9 Upper, front edge
10 Front edge
11 Lower, front corner
12 Lower edge
13 Rear edge
14 First recess
15 Second recess
16 First axle
17 Second axle
18 Third axle
19 Fourth Axle
20 Spring
21 Spring
22 Enclosure
23 Cover
24 Electric Motor
25 Transmission output shaft
26 First bevel gear
27 Second bevel gear
28 Thickening
29 Proximal end of the enclosure
30 Rounding of the enclosure
31 Distal end of the enclosure
32 Head screw gear
33 Head screw gear segment
34 First joint axis
35 Gear segment
36 Drive shaft
37 Guide
38 Kernel
39 Scraper
40 Slide surface/lock cover
41 Fingertip

The invention claimed is:

1. A finger element comprising:
a "U" shaped basic element having plate shaped segments that surround and pivotably supports an end of a first finger limb, so that the first finger limb is pivotable to and fro in a pivoting direction with respect to the basic element,
an electric motor being contained within the first finger limb for moving the first finger limb relative to the basic element,
a transmission coupling the electric motor to the basic element,
a control and regulating element for controlling and regulating, by a current characteristic, a current which is supplied to the electric motor for controlling movement of the first finger limb,
the control and regulating element supplying the electric motor with a current for moving the first finger limb, to and fro in the pivoting direction, and for position holding of the first finger limb relative to the basic element, and the controlled and regulated current characteristic for the holding of the first finger limb is supplied in such a way that the electric motor receives a supplied current which is greater than zero and less than a supplied current required for moving the first finger limb relative to the basic element, and
if an external force in either of the pivoting directions is applied to the first finger limb, which is greater than a force being applied by the electric motor in the pivoting direction for either moving or holding the first finger limb in a desired position, the external force in the pivoting direction overcomes the force applied by the electric motor and moves the first finger limb, regardless of the direction of the force being provided by the electric motor, without damaging the electric motor or the transmission.

2. The finger element according to claim 1, wherein the current characteristic comprises at least one of a current intensity, a voltage and a frequency.

3. The finger element according to claim 1, wherein the electric motor is functionally connected by the transmission which comprises a first bevel gear meshing with a second bevel gear, and the second bevel gear is fixedly positioned, relative to the first finger limb, and the rotation axis of the second bevel gear is the pivoting axis of the first finger limb.

4. The finger element according to claim 3, wherein the rotation axis of the second bevel gear is vertically positioned with reference to the rotation axis of the first bevel gear.

5. The finger element according to claim 3, wherein the rotation axis of the second bevel gear has an offset in a plane with reference to the rotation axis of the first bevel gear so that the rotation axes do not intersect.

6. The finger element according to claim 1, wherein the transmission is located directly between the first finger limb and the basic element and directly couples the electric motor to the first finger limb.

7. The finger element according to claim 1, wherein the basic element is designed to be attached directly to a human body part, and the first finger limb is an intermediate limb that is coupled to the basic element.

8. The finger element according to claim 7, wherein the intermediate limb is pivotable connected, at a first end thereof, to the basic element and pivotably connected, at a second end thereof, to a second finger limb.

9. The finger element according to claim 8, wherein the second finger limb is connected to the basic element by a spring.

10. The finger element according to claim 1, wherein the first finger limb further comprises an enclosure and a cover; and the transmission comprises a transmission output shaft, a first bevel gear and a second bevel gear which cooperate with one another to provide the pivoting movement of the first finger limb relative to the basic element.

11. The finger element according to claim 1, wherein electric braking of the electric motor retains the first finger limb for position holding of the first finger limb in a stationary position.

12. The finger element according to claim 11, wherein the electric braking comprises the control and regulating element supplying the electric motor with the current that is greater than zero and less than 0.1 times the current required for moving the first finger limb.

13. The finger element according to claim 1, wherein the supplied current, required for position holding of the first finger limb, is less than the supplied current, required for moving the first finger limb relative to the basic element, and the supplied current required for position holding of the first finger limb is greater than zero and less than 0.9 times the supplied current required for moving the first finger limb.

14. The finger element according to claim 1, wherein the supplied current, required for position holding of the first finger limb, is less than the supplied current, required for moving the first finger limb relative to the basic element, and the supplied current required for position holding of the first finger limb is greater than zero and less than 0.5 times the supplied current required for moving the first finger limb.

15. The finger element according to claim 1, wherein the supplied current, required for position holding of the first finger limb, is less than the supplied current required for moving the first finger limb relative to the basic element, and the supplied current required for position holding of the first finger limb is greater than zero and less than 0.1 times the supplied current required for moving the first finger limb.

16. A prosthesis comprising at least a first finger limb and an electric motor, positioned within the first finger limb, for driving the first finger limb, and a prosthesis "U" shaped basic element around which the first finger limb pivots to and fro in a pivoting direction, wherein a transmission is drivingly located between the first finger limb and the basic element, the transmission couples the electric motor to the basic element for moving the first finger limb relative to the basic element, and the electric motor is contained within the first finger limb, a control and regulating element for controlling and regulating, by a current characteristic, a current which is supplied to the electric motor for controlling movement of the first finger limb, the control and regulating element supplying the electric motor with a first current for moving the first finger, and a second current, which is greater than zero and less than a supplied current required for moving the first finger limb relative to the basic element, for position holding of the first finger limb relative to the basic element, and if an external force in either of the pivoting directions is applied to the first finger limb, which is greater than a force being applied by the electric motor in the pivoting direction for either moving or holding the first finger limb in a desired position, the external force in the pivoting direction overcomes the force applied by the electric motor and moves the first finger limb, regardless of the direction of the force being provided by the electric motor, without damaging the electric motor or the non-locking transmission.

17. A finger element comprising:

a U-shaped basic element having a pair of spaced apart plate shaped segments, a first end of a first finger limb being located between the pair of plate shaped segments and the first finger limb being supported by the plate shaped segments so as to be pivotable with respect to the basic element to and fro in a pivoting direction, an electric motor being contained within the first finger limb for moving the first finger limb relative to the basic element, a transmission coupling the electric motor to the basic element, a control and regulating element for controlling and regulating, by a current characteristic, a current which is supplied to the electric motor for controlling to and fro movement of the first finger limb, the control and regulating element supplying the electric motor with a current for both moving and for holding of the first finger limb relative to the basic element, and the controlled and regulated current is supplied to the electric motor in such a way that the electric motor is:

supplied with a greater current, in order to move the first finger limb relative to the basic element, and supplied with a lesser current, in order to hold the first finger limb relative to the basic element, and the lesser current greater than zero is less than 0.5 times the current required to move the first finger limb position relative to the basic element;

wherein if an external force in the pivoting direction is applied to the first finger limb, which is greater than a force being applied by the electric motor in the pivoting direction for either moving or holding the first finger limb in a desired position, the external force in the pivoting direction overcomes the force applied by the electric motor and moves the first finger limb, regardless of the direction of the force being provided by the electric motor, without damaging the electric motor or the transmission.

* * * * *